(12) United States Patent
Meertens et al.

(10) Patent No.: US 9,182,786 B2
(45) Date of Patent: Nov. 10, 2015

(54) SYSTEM COMPRISING A DOCKING STATION AND A HANDHELD DEVICE

(75) Inventors: Wendela Meertens, Eindhoven (NL); Tom Philippe Jean Jacques Delaey, Mol (BE)

(73) Assignee: Koninklijke Philips N.V., Eindhoven (NL)

( * ) Notice: Subject to any disclaimer, the term of this patent is extended or adjusted under 35 U.S.C. 154(b) by 87 days.

(21) Appl. No.: 13/878,949

(22) PCT Filed: Oct. 14, 2011

(86) PCT No.: PCT/IB2011/054560
§ 371 (c)(1),
(2), (4) Date: Apr. 11, 2013

(87) PCT Pub. No.: WO2012/052895
PCT Pub. Date: Apr. 26, 2012

(65) Prior Publication Data
US 2013/0208416 A1    Aug. 15, 2013

(30) Foreign Application Priority Data
Oct. 18, 2010  (EP) ..................................... 10187848

(51) Int. Cl.
| A61B 5/00 | (2006.01) |
| G06F 1/16 | (2006.01) |
| H05K 5/00 | (2006.01) |
| H05K 7/00 | (2006.01) |
| G01N 33/487 | (2006.01) |
| G12B 9/08 | (2006.01) |

(52) U.S. Cl.
CPC ........ *G06F 1/1632* (2013.01); *G01N 33/48785* (2013.01); *G12B 9/08* (2013.01)

(58) Field of Classification Search
None
See application file for complete search history.

(56) References Cited

U.S. PATENT DOCUMENTS

| 5,882,602 | A |   | 3/1999  | Savage |
| D441,867  | S |   | 5/2001  | Belisle |
| D462,771  | S |   | 9/2002  | Weber |
| D548,690  | S | * | 8/2007  | Aglassinger ................. D13/108 |
| 7,488,216 | B2 | * | 2/2009  | Cho .............................. 439/638 |
| 7,735,536 | B2 |   | 6/2010  | Mukai |
| 7,782,610 | B2 | * | 8/2010  | Diebel et al. ............. 361/679.56 |
| 7,805,135 | B2 | * | 9/2010  | Struthers et al. ........... 455/422.1 |
| 7,818,132 | B2 | * | 10/2010 | Pritchard et al. ................ 702/23 |
| 7,883,015 | B2 | * | 2/2011  | Ackermann et al. .......... 235/439 |
| 7,969,732 | B1 | * | 6/2011  | Noble ...................... 361/679.56 |
| 8,077,453 | B2 | * | 12/2011 | Swan et al. ............... 361/679.41 |
| 8,325,476 | B2 | * | 12/2012 | Huang et al. ............. 361/679.41 |
| RE44,345  | E  | * | 7/2013  | Ackermann et al. .......... 235/439 |
| 8,939,373 | B2 | * | 1/2015  | Kawabata et al. ........ 235/462.13 |
| 2001/0003071 | A1 | * | 6/2001 | Mansutti et al. .............. 439/133 |
| 2002/0060247 | A1 | * | 5/2002 | Krishnaswamy et al. ......................... 235/472.01 |
| 2002/0170823 | A1 | * | 11/2002 | Housefield et al. ....... 204/403.01 |
| 2003/0218445 | A1 | * | 11/2003 | Behar ........................... 320/114 |
| 2004/0212344 | A1 | * | 10/2004 | Tamura et al. ................ 320/114 |
| 2006/0221565 | A1 | * | 10/2006 | Doherty et al. ............... 361/683 |

(Continued)

FOREIGN PATENT DOCUMENTS

WO    2005105414 A1    11/2005

*Primary Examiner* — Hoa C Nguyen
*Assistant Examiner* — Xanthia C Cunningham

(57) ABSTRACT

A system includes a docking station and a handheld device. The docking station has four walls and a bathtub shape following the contours of the handheld device tightly. The inner part of the four walls is curved so that the handheld device is guided during docking.

17 Claims, 1 Drawing Sheet

(56) References Cited

U.S. PATENT DOCUMENTS

| | | | |
|---|---|---|---|
| 2006/0229502 A1* | 10/2006 | Pollock et al. | 600/300 |
| 2006/0245131 A1* | 11/2006 | Ramey et al. | 361/90 |
| 2006/0258929 A1* | 11/2006 | Goode et al. | 600/345 |
| 2007/0002533 A1* | 1/2007 | Kogan et al. | 361/686 |
| 2008/0031780 A1* | 2/2008 | Larsen | 422/82.01 |
| 2008/0108884 A1* | 5/2008 | Kiani | 600/301 |
| 2008/0221930 A1* | 9/2008 | Wekell et al. | 705/3 |
| 2008/0273734 A1 | 11/2008 | Solland | |
| 2009/0009957 A1* | 1/2009 | Crooijmans et al. | 361/686 |
| 2009/0227855 A1* | 9/2009 | Hill et al. | 600/365 |
| 2009/0299301 A1* | 12/2009 | Gottlieb et al. | 604/263 |
| 2010/0069730 A1* | 3/2010 | Bergstrom et al. | 600/365 |
| 2010/0121164 A1* | 5/2010 | Donars et al. | 600/323 |
| 2010/0179408 A1* | 7/2010 | Kamath et al. | 600/365 |
| 2010/0195279 A1* | 8/2010 | Michael | 361/679.41 |
| 2010/0198142 A1* | 8/2010 | Sloan et al. | 604/66 |
| 2010/0261979 A1* | 10/2010 | Kiani | 600/301 |
| 2010/0268052 A1* | 10/2010 | Asama et al. | 600/365 |
| 2010/0331652 A1* | 12/2010 | Groll et al. | 600/365 |
| 2011/0075349 A1* | 3/2011 | Ma et al. | 361/679.41 |
| 2011/0119074 A1* | 5/2011 | Drucker et al. | 705/2 |
| 2011/0164365 A1* | 7/2011 | McClure et al. | 361/679.3 |
| 2011/0208076 A1* | 8/2011 | Fong et al. | 600/509 |
| 2011/0313395 A1* | 12/2011 | Krulevitch et al. | 604/504 |

* cited by examiner

SYSTEM COMPRISING A DOCKING STATION AND A HANDHELD DEVICE

FIELD OF THE INVENTION

The invention relates to a system comprising a docking station for docking with a handheld device and said handheld device.

BACKGROUND OF THE INVENTION

U.S. Pat. No. D4,627,771 S shows a docking station for docking with a glucose testing instrument. The instrument lies flat on the docking station. The disadvantage of this docking station is that it is not that easy for a user to place the instrument in the docking station and that this might require several tries.

SUMMARY OF THE INVENTION

It is a first object of the invention to provide a system of the type described in the opening paragraph, which allows a user to place the handheld device in the docking station with less effort.

According to the invention, the first object is realized in that the device has a bathtub shape following the contours of the handheld device tightly and comprises four walls, the inner part of the four walls being curved so that the handheld device is guided during docking. The curved walls guide the handheld device in the docking station, thereby allowing a user to place the handheld device in the docking station with less effort. If the user does not place the handheld device at the right position in the docking station, the handheld device automatically slides into this right position. When using a physical connector, the only handling that a user needs to do after positioning the handheld device is pressing slightly at the handheld device to make the physical connection without applying pressure on the handheld device or physical connector.

In an embodiment, the height of the walls is chosen such that the top side of the walls is higher than or of the same height as the center of gravity of the handheld device when the handheld device is docked in the docking station. This ensures that the handheld device does not easily fall out of the docking station when the docking station is being moved, e.g. in hospitals or ambulances.

The height of the walls may be between 20 mm and 30 mm and the center of gravity of the handheld device may accordingly be positioned at maximum 25 mm of the bottom surface of the handheld device. These dimensions ensure that the handheld device does not easily fall out of the docking station when the docking station is being moved, but that the handheld device is still easy to grab from the docking station.

The height of the walls may be 25 mm. This height is very favorable if the center of gravity of the handheld device is positioned at 25 mm of the bottom surface of the handheld device.

The handheld device may be 50 mm high. In order to be able to position the center of gravity of the handheld device at maximum 25 mm of the bottom surface of the handheld device, 50 mm is a convenient height for the handheld device.

A space may exist at the front side of the docking station between the handheld device and the docking station and the center of gravity of the handheld device may accordingly be positioned at the front half of the handheld device. This makes a small rotation of the instrument possible, thereby making undocking easy. The small space also makes handling of the handheld device easy, because it prevents vacuum formation between docking station and handheld device.

The docking station may further comprise at least one weight. This increases the weight of the docking station for easy handling when picking up the handheld device from the docking station. The extra weight prevents that a release button is required to undock the handheld device. The extra weight prevents that the physical connection is not released sufficiently and the docking station moves when the user picks up the handheld device if no release button is used.

The handheld device may be an analyzer, e.g. a blood analyzer. The handheld device may be part of a point-of-care biosensor system.

BRIEF DESCRIPTION OF THE DRAWINGS

These and other aspects of the invention are apparent from and will be further elucidated, by way of example, with reference to the drawings, in which.

Corresponding elements in the drawings are denoted by the same reference numeral.

DETAILED DESCRIPTION OF THE DRAWINGS

Figure 1:
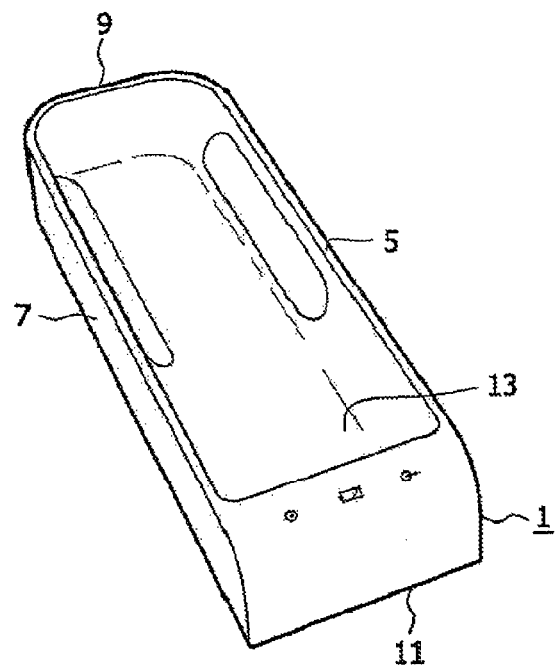
FIG. 1 is a perspective view of a first embodiment of the docking station.
Figure 2:
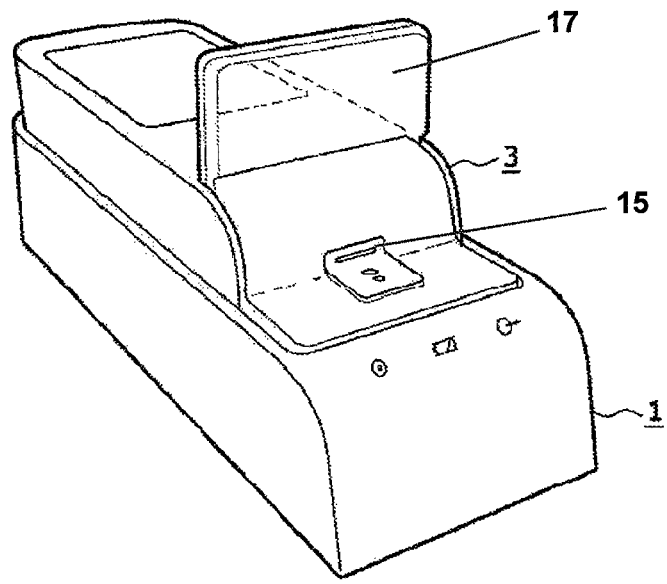
FIG. 2 is a perspective view of a first embodiment of the system.

The system comprises a docking station 1 for docking with a handheld device 3 and said handheld device 3, see FIG. 2. The docking station has a bathtub shape following the contours of the handheld device 3 tightly and comprises four walls 5, 7, 9, and 11, see FIG. 1. The inner part of the four walls 5, 7, 9, and 11 is curved so that the handheld device 3 is guided during docking.

In the embodiment shown in FIGS. 1 and 2, the handheld device 3 is an analyzer, e.g. a blood analyzer. In this embodiment, the height of the walls of the docking station is 25 mm and the handheld device is 50 mm high. The handheld device 3 includes a processing unit, a display and multiple buttons. Furthermore, a rotatable cover 15 and a slot 17 for inserting a cartridge containing a sample are included at the bottom of the handheld device 3. The slot 17 is positioned at such a height that the cartridge can be inserted while the handheld device 3 is docked in the docking station 1. The docking station 1 includes multiple indicators, including an indicator of battery power remaining. The docking station 1 has an extrusion at each of walls 5 and 7. These extrusions match corresponding indentations in the handheld device 3. These indentations provide a better grip of the handheld device. The docking station 1 and the handheld device 3 may communicate through a physical or wireless connection. In case of a wireless connection, the handheld device 3 may be charged via the docking station 1 by using wireless power. In case of a physical connection, the docking station 1 may comprise a connector and the handheld device 3 a socket or vice versa.

A space 13 exists at the front side of the docking station 1 between the handheld device 3 and the docking station 1 and the center of gravity of the handheld device 3 is positioned at the front half of the handheld device 3. This makes a small rotation of the handheld device 3 possible, thereby making undocking easy. The small space also makes handling of the handheld device 3 easy, because it prevents vacuum formation between docking station 1 and handheld device 3.

While the invention has been described in connection with preferred embodiments, it will be understood that modifications thereof within the principles outlined above will be evident to those skilled in the art, and thus the invention is not limited to the preferred embodiments but is intended to encompass such modifications. The invention resides in each and every novel characteristic feature and each and every combination of characteristic features. Reference numerals in the claims do not limit their protective scope. Use of the verb "to comprise" and its conjugations does not exclude the presence of elements other than those stated in the claims. Use of the article "a" or "an" preceding an element does not exclude the presence of a plurality of such elements.

'Means', as will be apparent to a person skilled in the art, are meant to include any hardware (such as separate or integrated circuits or electronic elements) or software (such as programs or parts of programs) which perform in operation or are designed to perform a specified function, be it solely or in conjunction with other functions, be it in isolation or in co-operation with other elements. The invention can be implemented by means of hardware comprising several distinct elements, and by means of a suitably programmed computer. The mere fact that certain measures are recited in mutually different dependent claims does not indicate that a combination of these measures cannot be used to advantage.

The invention claimed is:

1. A system comprising:
   a handheld device having a front surface, a back surface and four side walls between the front and back surfaces; and
   a docking station for docking with the handheld device,
   wherein the docking station has a bathtub shape following contours of the back surface of the handheld device tightly and comprises four walls,
   wherein inner parts of the four walls are curved so that the handheld device is guided during docking,
   wherein at least three side walls of the four side walls of the handheld device tightly contact at least three walls of the four walls of the docking station when the handheld device is docked in the docking station to prevent spaces between the at least three side walls and the at least three walls, and
   wherein the handheld device has a slot for inserting a cartridge containing a sample, the slot being positioned at such a height that the cartridge can be inserted into the slot while the handheld device is docked in the docking station.

2. The system as claimed in claim 1, wherein heights of the four walls are configured such that top sides of the four walls are higher than or of a same height as a center of gravity of the handheld device when the handheld device is docked in the docking station.

3. The system as claimed in claim 2, wherein the heights of the four walls are between 20 mm and 30 mm and the center of gravity of the handheld device is positioned at maximum of 25 mm from the back surface of the handheld device.

4. The system as claimed in claim 3, wherein the heights of the four walls are 25 mm.

5. The system as claimed in claim 3, wherein the handheld device is 50 mm high.

6. The system as claimed in claim 1, wherein a fourth wall of the four walls is located at a front of the docking station for receiving the handheld device, wherein when the handheld device is docked in the docking station the handheld device and the front of the docking station are not in contact with each other, and wherein a center of gravity of the handheld device is positioned at a front half of the handheld device located nearer to the front of the docking station than a back of the docking station opposite the front of the docking station.

7. The system as claimed in claim 1, wherein the docking station further comprises at least one weight.

8. The system as claimed in claim 1, wherein the handheld device comprises an analyzer.

9. The system as claimed in claim 1, wherein the docking station further comprises an extrusion at opposite walls, wherein the handheld device comprises gripping indentations, and wherein the extrusions match the gripping indentations.

10. The system of claim 1, wherein the handheld device has a display at an upper part of the front surface and a rotatable cover at a lower part of the front surface opposite the upper part, and wherein the lower part has the slot for inserting the cartridge containing the sample, wherein the slot is positioned at a height of the four walls of the docking station when the handheld device is docked in the docking station, and wherein the display is positioned at a height higher than the height of the four walls when the handheld device is docked in the docking station.

11. The system of claim 1, wherein the four wall of the docking station have a same height.

12. A docking station comprising:
   a surface; and
   four walls extending from the surface,
   wherein the docking station is configured to receive a handheld device having a front surface, a back surface and four side walls between the front and back surfaces,
   wherein the docking station has a bathtub shape following contours of the back surface of the handheld device tightly and comprises four walls,
   wherein inner parts of the four walls are curved so that the handheld device is guided during docking,
   wherein at least three side walls of the four side walls of the handheld device tightly contact at least three walls of the four walls of the docking station when the handheld device is docked in the docking station to prevent spaces between the at least three side walls and the at least three walls, and
   wherein the handheld device has a slot for inserting a cartridge containing a sample, the slot being positioned at such a height that the cartridge can be inserted into the slot while the handheld device is docked in the docking station.

13. The docking station of claim 12, wherein heights of the four walls are configured such that top sides of the four walls are higher than or of a same height as a center of gravity of the handheld device when the handheld device is docked in the docking station.

14. The docking station of claim 13, wherein the heights of the four walls are between 20 mm and 30 mm and the center of gravity of the handheld device is positioned at maximum of 25 mm from the back surface of the handheld device.

15. The docking station of claim 13, wherein the heights of the four walls are 25 mm, and wherein the handheld device is 50 mm high.

16. The docking station of claim 12, further comprising extrusions at two opposite walls of the four walls, wherein the handheld device comprises gripping indentations, and wherein the extrusions match the gripping indentations.

17. The docking station of claim 12, wherein the four wall of the docking station have a same height.

* * * * *